US 6,689,587 B2

(12) United States Patent
Bastuck et al.

(10) Patent No.: US 6,689,587 B2
(45) Date of Patent: Feb. 10, 2004

(54) POLYNUCLEOTIDES ENCODING THE NADC GENE AND METHODS OF PRODUCING NICOTINIC ACID OR NICOTINIC ACID DERIVATIVES

(75) Inventors: Christine Bastuck, Bielefeld (DE); Brigitte Bathe, Salzkotten (DE); Nicole Dusch, Bielefeld (DE); Bettina Moeckel, Duesseldorf (DE); Georg Thierbach, Bielefeld (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/789,582

(22) Filed: Feb. 22, 2001

(65) Prior Publication Data

US 2002/0137169 A1 Sep. 26, 2002

(30) Foreign Application Priority Data

Nov. 10, 2000 (DE) .......................... 100 55 870

(51) Int. Cl.[7] .......................... C12P 17/12; C12N 15/54; C12Q 1/68
(52) U.S. Cl. .......................... 435/122; 435/6; 435/194; 435/320.1; 435/252.3; 536/23.2; 536/24.33
(58) Field of Search .............................. 435/194, 320.1, 435/252.3, 122, 6; 536/23.2, 24.33

(56) References Cited

U.S. PATENT DOCUMENTS 3,650,898 A 3/1972 Nakayama et al. ....... 195/28 N
2002/0197605 A1 * 12/2002 Nakagawa et al. ............. 435/6

FOREIGN PATENT DOCUMENTS

| EP | 1108790 A2 | 6/2001 |
|---|---|---|
| JP | 3-280892 | 12/1991 |
| WO | WO 98/56923 | 12/1998 |
| WO | WO 01/00802 | 1/2001 |
| WO | WO 01/00843 | 1/2001 |
| WO | WO 01/00845 | 1/2001 |
| WO | WO 01/00847 | 1/2001 |

OTHER PUBLICATIONS

Tettelin, H., et al. (2000) Acc. No. AE002486.*
Adams, M., et al. (1999) Acc. No. AC017396.*
Birren, B., et al. (2000) Acc. No. AC009692.*
Acc. No. AAV84483 (1999).*
Shin–Ichi Fukuoka, et al., Biochimica et Biophysica Acta, vol. 1395, No. 2, pp. 192–201, XP–002192519, "Characterization and Functional Expression of the cDNA Encoding Human Brain Quinolinate Phosphoribosyltransferase", Jan. 21, 1998.
R. Bhatia, et al., Archives of Biochemistry and Biophysics, vol 325, No. 2, pp. 270–278, XP–002192520, "The Sequencing, Expression, Purification, and Steady–State Kinetic Analysis of Quinolinate Phosphoribosyl Transferase From *Escherichia coli*", Jan. 15, 1996.

* cited by examiner

Primary Examiner—Charles L. Patterson, Jr.
(74) Attorney, Agent, or Firm—Oblon, Spivak, McClelland, Maier & Neustadt, P.C.

(57) ABSTRACT

The present invention relates to polynucleotides corresponding to the nadC gene and which encode the nicotinate nucleotide pyrophosphorylase protein, methods of producing nicotinic acid or nicotinic acid derivatives, and methods of screening for polynucleotides which encode proteins having nicotinate nucleotide pyrophosphorylase activity.

52 Claims, 1 Drawing Sheet

POLYNUCLEOTIDES ENCODING THE NADC GENE AND METHODS OF PRODUCING NICOTINIC ACID OR NICOTINIC ACID DERIVATIVES

BACKGROUND OF THE INVENTION

1. Field of the Invention

The present invention relates to polynucleotides corresponding to the nadC gene and which encode the nicotinate nucleotide pyrophosphorylase protein, methods of producing nicotinic acid or nicotinic acid derivatives, and methods of screening for polynucleotides which encode proteins having nicotinate nucleotide pyrophosphorylase protein activity.

2. Discussion of the Background

Nicotinic acid and nicotinic acid derivatives are used in human medicine, in the pharmaceuticals industry, in the foodstuffs industry and in animal nutrition. It is known that L-amino acids are prepared by fermentation from strains of coryneform bacteria, in particular *Corynebacterium glutamicum*. Prior to the present invention there were no processes for the preparation of nicotinic acid or nicotinic acid derivatives using coryneform bacteria.

SUMMARY OF THE INVENTION

The inventors had the object of providing processes for the fermentative preparation of nicotinic acid and nicotinic acid derivatives.

Accordingly, one object of the present invention is an isolated polynucleotide which encodes a protein comprising the amino acid sequence of SEQ ID NO:2.

Another object of the present invention is the nucleotide sequence of SEQ ID NO:1.

Another object of the present invention are isolated polynucleotides which are complimentary to SEQ ID NO:1 or a 70%, 80% or 90% identical to SEQ ID NO:1.

Another object of the present invention are isolated polynucleotides which hybridizes under stringent conditions to SEQ ID NO:1.

Another object of the present invention are polynucleotides which comprises at least 15 consecutive nucleotides of SEQ ID NO:1.

Another object of the present invention are vectors and host cells containing the polynucleotides. In a preferred embodiment the host cells are Corynebacterium and are preferably *Corynebacterium glutamicum*.

Another object of the present invention is a Coryneform bacterium which has an enhanced nadC gene.

Another object of the present invention is to a process for producing nicotinic acid or a nicotinic acid derivative culturing a host cell in accordance with the invention in a medium suitable for the expression of the polynucleotide; and collecting the nicotinic acid or nicotinic acid derivative. In a preferred embodiment, the nicotinic acid or nicotinic acid derivative is concentrated after it is collected. In another embodiment, the host cell can also contain an pyc, zwa1 and/or prs whose expression is enhanced; and/or an pck, poxB and zwa2 whose expression is attenuated.

Another object of the present invention is a process for screening for polynucleotides which encode a protein having nicotinate nucleotide pyrophosphorylase protein activity by hybridizing one or more of the polynucleotides embodied in this application to the polynucleotide to be screened; expressing the polynucleotide to produce a protein; and detecting the presence or absence of nicotinate nucleotide pyrophosphorylase protein activity in said protein.

DETAILED DESCRIPTION OF THE INVENTION

Figure 1:
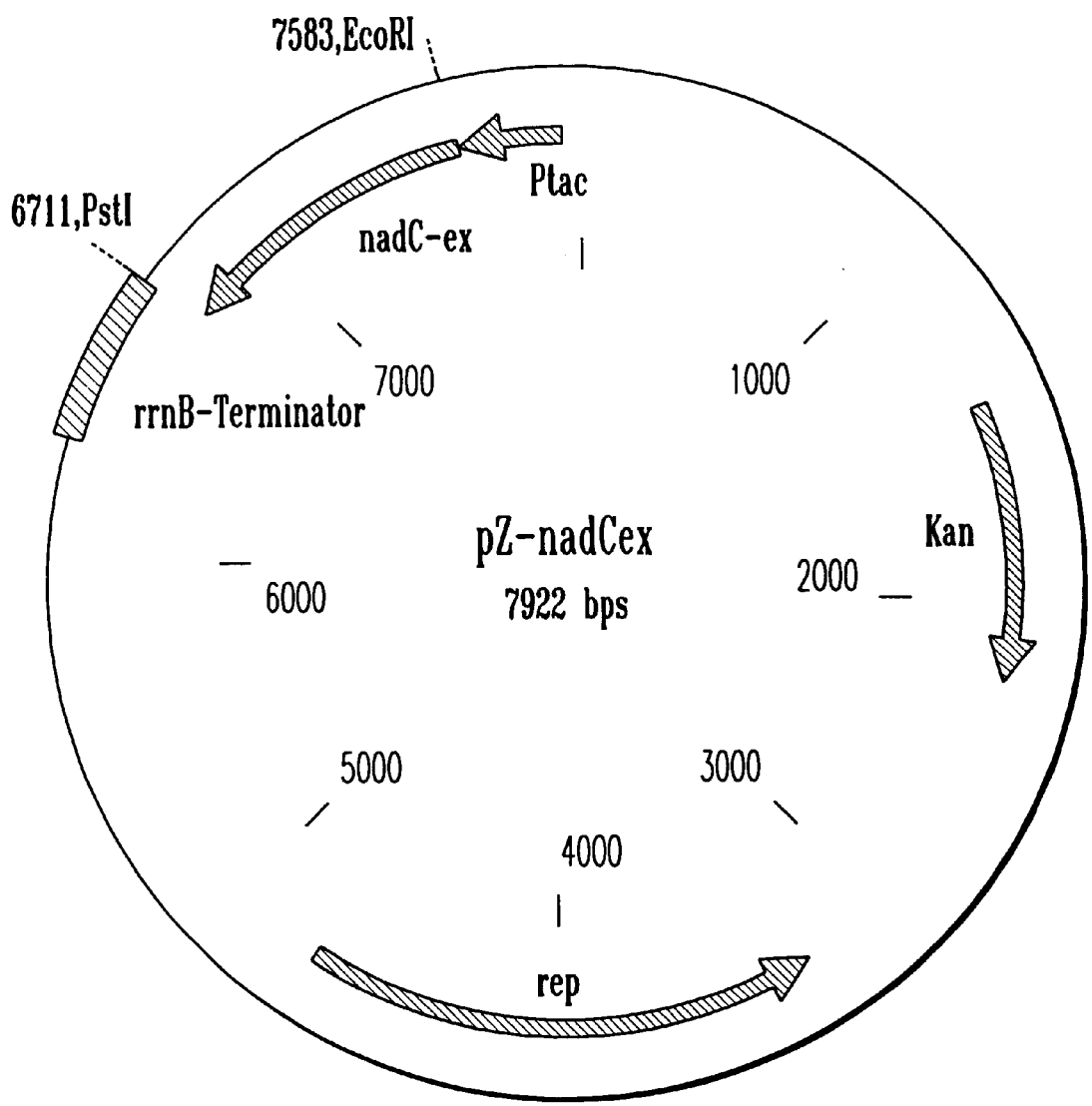
FIG. 1: Map of the plasmid pZ-nadCex

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory, New York (1982) and Sambrook et al., Molecular Cloning: A Laboratory Manual, Cold Spring Harbor Laboratory, New York (1989) and the various references cited therein.

"Nicotinic acid or nicotinic acid derivatives" as used herein is understood to mean one or more compounds, including their salts, chosen from nicotinic acid, nicotinamide, quinolinic acid (quinolinate), nicotinic acid mononucleotide, nicotinic acid adenine dinucleotide, nicotinamide adenine dinucleotide (NAD) and nicotinamide adenine dinucleotide phosphate (NADP). Nicotinic acid is particularly preferred.

The invention also provides polynucleotides which substantially comprise a polynucleotide sequence, which are obtainable by screening by means of hybridization of a corresponding gene library of a coryneform bacterium, which comprises the complete gene or parts thereof, with a probe which comprises the sequence of the polynucleotide according to the invention according to SEQ ID NO:1 or a fragment thereof, and isolation of the polynucleotide sequence mentioned.

Polynucleotides which comprise the sequences according to the invention are suitable as hybridization probes for RNA, cDNA and DNA, in order to isolate, in the full length, nucleic acids or polynucleotides or genes which code for quinolinate synthetase or to isolate those nucleic acids or polynucleotides or genes which have a high similarity with the sequence of the nadA gene. They are also suitable for incorporation into so-called "arrays", micro arrays" or DNA chips" in order to detect and determine the corresponding polynucleotides.

Polynucleotides which comprise the sequences according to the invention are furthermore suitable as primers with the aid of which DNA of genes which code for nicotinate nucleotide pyrophosphorylase can be prepared by the polymerase chain reaction (PCR). Such polynucleotides or oligonucleotides which serve as probes or primers comprise at least 25, 26, 27, 28, 29 or 30, preferably at least 20, 21, 22, 23 or 24 very particularly preferably at least 15, 16, 17, 18 or 19 successive nucleotides. Oligonucleotides with a length of at least 31, 32, 33, 34, 35, 36, 37, 38, 39 or 40 or at least 41, 42, 43, 44, 45, 46, 47, 48, 49 or 50 nucleotides are also suitable. Oligonucleotides with a length of at least 100, 150, 200, 250 or 300 nucleotides are optionally also suitable.

"Isolated" means separated out of its natural environment.

As used herein "Ptac" is understood to meant Ptac promoter; "rep" is understood to mean plasmid-coded replication region from *C. glutamicum* plasmid pGA1; "rrnB" is understood to mean terminator T1T2 of the rmB gene of *E.coli*; "Kan" is understood to mean a resistance gene for kanamycin; "nadC-ex" is understood to mean nadCgene of *C. glutamicum* without promoter region; "EcoRI" is understood to mean a cleavage site of the restriction enzyme EcoRI; and "PstI" is understood to mean a cleavage site of the restriction enzyme PstI.

"Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID No. 1 or a fragment prepared therefrom and also those which are at least 70% to 80%, preferably at least 81% to 85%, particularly preferably at least 86% to 90% and very particularly preferably at least 91%, 93%, 95%, 97% or 99% identical to the polynucleotide according to SEQ ID No. 1 or a fragment prepared therefrom.

"Polypeptides" are understood as meaning peptides or proteins which comprise two or more amino acids bonded via peptide bonds.

The polypeptides according to the invention include a polypeptide according to SEQ ID No. 2, in particular those with the biological activity of nicotinate nucleotide pyrophosphorylase, and also those which are at least 70% to 80%, preferably at least 81% to 85% and particularly preferably at least 86% to 90% and very particularly preferably at least 91%, 93%, 95%, 97% or 99% identical to the polypeptide according to SEQ ID No. 2 and have the activity mentioned.

The invention also relates to a process for the fermentative preparation of nicotinic acid or nicotinic acid derivatives chosen from the group consisting of nicotinic acid, nicotinamide, nicotinic acid mononucleotide, nicotinic acid adenine dinucleotide, nicotinamide adenine dinucleotide (NAD) and nicotinamide adenine dinucleotide phosphate (NADP) using coryneform bacteria in which the nucleotide sequences which code for the nadC gene are enhanced, in particular over-expressed.

The term "enhancement" in this connection describes the increase in the intracellular activity of one or more enzymes in a microorganism which are coded by the corresponding DNA, for example by increasing the number of copies of the gene or genes, using a potent promoter or using a gene which codes for a corresponding enzyme having a high activity, and optionally combining these measures.

The microorganisms which the present invention provides can produce nicotinic acid or nicotinic acid derivatives from glucose, sucrose, lactose, fructose, maltose, molasses, starch, cellulose or from glycerol and ethanol. They can be representatives of coryneform bacteria, in particular of the genus Corynebacterium. Of the genus Corynebacterium, there may be mentioned in particular the species *Corynebacterium glutamicum*, which is known among experts for its ability to produce L-amino acids.

Suitable strains of the genus Corynebacterium, in particular of the species *Corynebacterium glutamicum* (*C. glutamicum*), are in particular the known wild-type strains
Corynebacterium glutamicum ATCC13032
Corynebacterium acetoglutamicum ATCC15806
Corynebacterium acetoacidophilum ATCC 13870
Corynebacterium thermoaminogenes FERM BP-1539
Corynebacterium melassecola ATCC17965
Brevibacterium flavum ATCC14067
Brevibacterium lactofermentum ATCC13869 and
Brevibacterium divaricatum ATCC14020.

The isolated nadC gene from *C. glutamicum* which codes for the enzyme nicotinate nucleotide pyrophosphorylase (EC 2.4.2.19).

To isolate the nadC gene or also other genes of *C. glutamicum*, a gene library of this microorganism is first set up in *Escherichia coli* (*E. coli*). The setting up of gene libraries is described in generally known textbooks and handbooks. The textbook by Winnacker: Gene und Klone, Eine Einführung in die Gentechnologie [Genes and Clones, An Introduction to Genetic Engineering] (Verlag Chemie, Weinheim, Germany, 1990), or the handbook by Sambrook et al.: Molecular Cloning, A Laboratory Manual (Cold Spring Harbor Laboratory Press, 1989) may be mentioned as an example. A well-known gene library is that of the *E. coli* K-12 strain W3110 setup in λ vectors by Kohara et al. (Cell 50, 495–508 (1987)). Bathe et al. (Molecular and General Genetics, 252:255–265, 1996) describe a gene library of *C. glutamicum* ATCC13032, which was set up with the aid of the cosmid vector SuperCos I (Wahl et al., 1987, Proceedings of the National academy of Sciences, USA, 84:2160–2164) in the *E. coli* K-12 strain NM554 (Raleigh et al., 1988, Nucleic Acids Research 16:1563–1575).

Börmann et al. (Molecular Microbiology 6(3), 317–326) (1992)) in turn describe a gene library of *C. glutamicum* ATCC13032 using the cosmid pHC79 (Hohn and Collins, Gene 11, 291–298 (1980)).

To prepare a gene library of *C. glutamicum* in *E. coli* it is also possible to use plasmids such as pBR322 (Bolivar, Life Sciences, 25, 807–818 (1979)) or pUC9 (Vieira et al., 1982, lene, 19:259–268). Suitable hosts are, in particular, those *E. coli* strains which are restriction- and recombination-defective. An example of these is the strain DH5αmcr, which has been described by Grant et al. (Proceedings of the National Academy of Sciences USA, 87 (1990) 4645–4649). The long DNA fragments cloned with the aid of cosmids can in turn be subcloned in the usual vectors suitable for sequencing and then sequenced, as is described e.g. by Sanger et al. (Proceedings of the National Academy of Sciences of the United States of America, 74:5463–5467, 1977).

The resulting DNA sequences can then be investigated with known algorithms or sequence analysis programs, such as e.g. that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

The new DNA sequence of *C. glutamicum* which codes for the nadC gene and which, as SEQ ID No. 1, is a constituent of the present invention has been found. The amino acid sequence of the corresponding protein has furthermore been derived from the present DNA sequence by the methods described above. The resulting amino acid sequence of the nadC gene product is shown in SEQ ID No. 2. It is known that, during or after translation, enzymes endogenous in the host can split off the N-terminal amino acid methionine or formylmethionine from proteins formed.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. Such mutations are also called, inter alia, neutral substitutions. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994), in Hochuli et al. (Bio/Technology 6:1321–1325 (1988)) and in known textbooks of genetics and molecular biology. Amino acid sequences which result in a corresponding manner from SEQ ID No. 2 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) and in Liebl et al. (International Journal of Systematic Bacteriology (1991) 41: 255–260). The hybridization takes place under stringent conditions, that is to say only hybrids in which the probe and target sequence, i.e. the polynucleotides treated with the probe, are at least 70% identical are formed. It is known that the stringency of the hybridization, including the washing steps, is influenced or determined by varying the buffer composition the temperature and the salt concentration. The hybridization reaction is preferably carried out under a relatively low stringency compared with the washing steps (Hybaid Hybridisation Guide, Hybaid Limited, Teddington, UK, 1996).

A 5×SSC buffer at a temperature of approx. 50° C.–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridization, Boehringer Mannheim, Germany, 1995) a temperature of approx. 50° C.–68° C. being established. It is optionally possible to lower the salt concentration to 0.1×SSC. Polynucleotide fragments which are, for example, at least 70% or at least 80% or at least 90% to 95% or at least 96% to 99% identical to the sequence of the probe employed can be isolated by increasing the hybridization temperature stepwise from 50° C. to 68° C. in steps of approx. 1° C.–2° C. It is also possible to isolate polynucleotide fragments which are completely identical to the sequence of the probe employed. Further instructions on hybridization are obtainable on the market in the form of so-called kits (e.g. DIG Easy Hyb from Roche Diagnostics GmbH, Mannheim, Germany, Catalogue No. 1603558).

Instructions for amplification of DNA sequences with the aid of the polymerase chain reaction (PCR) can be found by the expert, inter alia, in the handbook by Gait: Oligonucleotide Synthesis: A Practical Approach (IRL Press, Oxford, UK, 1984) and in Newton and Graham: PCR (Spektrum Akademischer Verlag, Heidelberg, Germany, 1994).

It has been found that coryneform bacteria produce nicotinic acid in an improved manner after over-expression of the nadC gene.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative nicotinic acid production. The expression is likewise improved by measures to prolong the life of the m-RNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by the expert, inter alia, in Martin et al. (Bio/Technology 5, 137–146 (1987)), in Guerrero et al. (Gene 138, 35–41 (1994)), Tsuchiya ant Morinaga (Bio/Technology 6, 428–430 (1988)), in Eikmanns et al. (Gene 102, 93–98 (991)), in EP 0 472 86, in U.S. Pat. No. 4,601,893, in Schwarzer and P ühler (Bio/Technology 9, 84–87 (1991), in Reinscheid et al. (Applied and Environmental Microbiology 60, 126–132 (1994)), in LaBarre et al. (Journal of Bacteriology 175, 1001–1007 (1993)), in WO 96/15246, in Malumbres et al. (Gene 134, 15–24 (1993)), in JP-A-10-229891, in Jensen and Hammer (Biotechnology and Bioengineering 58, 191–195 (1998)), in Makrides (Microbiological Reviews 60:512–538 (1996)) and in known textbooks of genetics and molecular biology.

By way of example, for enhancement the nadC gene according to the invention was over-expressed with the aid of episomal plasmids. Suitable plasmids are those which are replicated in coryneform bacteria. Numerous known plasmid vectors, such as e.g. pZ1 (Menkel et al., Applied and Environmental Microbiology (1989) 64: 549–554), pEKEx1 (Eikmanns et al., Gene 102:93–98 (1991)) or pHS2-1 (Sonnen et al., Gene 107:69–74 (1991)) are based on the cryptic plasmids pHM1519, pBL1 or pGA1. Other plasmid vectors, such as e.g. those based on pCG4 (U.S. Pat. No. 4,489,160), or pNG2 (Serwold-Davis et al., FEMS Microbiology Letters 66, 119–124 (1990)), or pAG1 (U.S. Pat. No. 5,158,891), can be used in the same manner.

An example of such a plasmid is the plasmid pZ-nadCex1 shown in FIG. 1.

Plasmid vectors which are also suitable are also those with the aid of which the process of gene amplification by integration into the chromosome can be used, as has been described, for example, by Reinscheid et al. (Applied and Environmental Microbiology 60, 126–132 (1994)) for duplication or amplification of the hom-thrB operon. In this method, the complete gene is cloned in a plasmid vector which can replicate in a host (typically E. coli), but not in C. glutamicum. Possible vectors are, for example, pSUP301 (Simon et al., Bio/Technology 1, 784–791 (1983)), pK18mob or pK19mob (Schäfer et al., Gene 145, 69–73 (1994)), pGEM-T (Promega corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Holland; Bernard et al., Journal of Molecular Biology, 234: 534–541 (1993)), pEM1 (Schrumpf et al, 1991, Journal of Bacteriology 173:4510–4516) or pBGS8 (Spratt et al., 1986, Gene 41: 337–342). The plasmid vector which contains the gene to be amplified is then transferred into the desired strain of C. glutamicum by conjugation or transformation. The method of conjugation is described, for example, by Schäfer et al. (Applied and Environments Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross over" event, the resulting strain contains at least two copies of the gene in question.

In addition, it may be advantageous for the production of nicotinic acid or nicotinic acid derivatives to enhance, in particular over-express, one or more enzymes of glycolysis, of anaplerosis and optionally regulatory proteins, in addition to the nadC gene.

In a preferred embodiment of preparing nicotinic acid or nicotinic acid derivatives, in addition to enhancing the nadC gene, one or more of the following genes can be enhanced:
the pyc gene which codes for pyruvate carboxylase (DE-A-198 31 609);
the zwa1 gene which codes for the Zwa1 protein (DE: 199 59 328.0, DSM 13115); and/or
the prs gene which codes for phosphoribosyl pyrophosphate synthetase (ACCESSION No. U76387).

It may also be advantageous for the production of nicotinic acid or nicotinic acid derivatives, to attenuate or reduce the expression of one or more of the following genes:
the pck gene which codes for phosphoenol pyruvate carboxykinase (DE 199 50 409.1; DSM 13047);
the poxB gene which codes for pyruvate oxidase (DE: 199 51 975.7; DSM 13114); and/or
the zwa2 gene which codes for the Zwa2 protein (DE: 199 59 327.2, DSM 13113).

The term "attenuation" or "attenuating" in this connection describes the reduction or elimination of the intracellular activity of one or more enzymes (proteins) in a microorganims which are coded by the corresponding DNA, for example by using a weak promoter or using a gene or allele which codes for a corresponding enzyme with a low activity or inactivates the corresponding gene or enzyme (protein), and optionally combining these measures.

In addition to over-expression of the nadC gene it may furthermore be advantageous, for the production of nicotinic acid or nicotinic acid derivatives, to eliminate undesirable side reactions, (Nakayama: "Breeding of Amino Acid Producing Micro-organims", in: Overproduction of Microbial Products, Krumphanzl, Sikyta, Vanek (eds.), Academic Press, London, UK, 1982).

The invention also provides the microorganisms prepared according to the invention, and these can be cultured continuously or discontinuously in the batch process (batch culture) or in the fed batch (feed process) or repeated fed batch process (repetitive feed process) for the purpose of production of nicotinic acid. A summary of known culture methods is described in the textbook by Chmiel (Bioprozesstechnik 1. Einführung in die Bioverfahrenstechnik [Bioprocess Technology 1. Introduction to Bioprocess Technology] (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substance can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in suitable manner to control the pH. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of nicotinic acid or nicotinic acid derivatives are known from the prior art. The concentration of nicotinic acid or nicotinic acid derivatives formed can be determined with microbiological methods, such as, for example, the *Lactobacillus plantarum* test (DIFCO MANUAL, $10^{th}$ Edition, p. 1100–1102; Michigan, USA).

A pure culture of the *C. glutamicum* strain DSM12455/pZ-nadCex was deposited on Oct. 25, 2000 at the Deutsche Sammlung für Mikroorganismen und Zellkulturen (DSMZ=German Collection of Microorganisms and Cell Cultures, Braunschweig, Germany) in accordance with the Budapest Treaty as DSM 13793.

The process according to the invention is used for fermentative preparation of nicotinic acid and nicotinic acid derivatives.

The isolation of plasmid DNA from *Escherichia coli* and all techniques of restriction, Klenow and alkaline phosphatase treatment were carried out by the method of Sambrook et al. (Molecular Cloning. A Laboratory Manual (1989) Cold Spring Harbour Laboratory Press, Cold Spring Harbor, N.Y., USA). Methods for transformation of *Escherichia coli* are also described in this handbook.

The composition of the usual nutrient media, such as LB or TY medium, can also be found in the handbook by Sambrook et al.

The strain ATCC13032ΔilvA is deposited as DSM12455 at the Deutsche Sammlung für Mikroorganismen und Zellkulturen in Braunschweig (Germany) in accordance with the Budapest Treaty and is described in EP-A-1006189.

Having generally described this invention, a further understanding can be obtained by reference to certain specific examples which are provided herein for purposes of illustration only, and are not intended to be limiting unless otherwise specified.

EXAMPLES

Example 1

Preparation of a Genomic Cosmid Gene Library from *Corynebacterium glutamicum* ATCC 13032

Chromosomal DNA from *Corynebacterium glutamicum* ATCC 13032 is isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Diagnostics GmbH, Mannheim, Germany, Product Description SAP, Code no. 1758250). The DNA of the cosmid vector SuperCos1 (Wahl et al. (1987) Proceedings of the National Academy of Sciences USA 84:2160–2164), obtained from Stratagene (La Jolla, USA, Product Description SuperCos1 Cosmid Vektor Kit, Code no. 251301) is cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA is then cleaved with the restriction enzyme BamHI (Amershar Pharmacia, Freiburg, Germany, Product Description BamHI, Code no. 27-0868-04). The cosmid DNA treated in this manner is mixed with the treated ATCC13032 DNA and the batch is treated with T4 DNA ligase (Amersham Pharmacia, Freiburg, Germany, Product Description T4-DNA-Ligase, Code no.27-0870-04). The ligation mixture is then packed in phages with the aid of Gigapack II XL Packing Extract (Stratagene, La Jolla, USA, Product Description Gigapack II XL Packing Extract, Code no. 200217).

For infection of the *E. coli* strain NM554 (Raleigh et al. 1988, Nucleic Acid Research 16:1563–1575) the cells are taken up in 10 mM $MgSO_4$ and mixed with an aliquot of the phage suspension. The infection and titering of the cosmid library are carried out as described by Sambrook et al. (1989, Molecular Cloning: A Laboratory Manual, Cold Spring Harbor), the cells being plated out on LB agar (Lennox, 1955, Virology, 1:190) with 100 mg/l ampicillin. After incubation overnight at 37° C., recombinant individual clones can be selected.

Example 2
Isolation and Sequencing of the nadC Gene

The cosmid DNA of an individual colony is isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments are dephosphorylated with shrimp alkaline phosphatase (Roche Diagnostics GmbH, Mannheim, Germany, Product Description SAP, Product No. 1758250). After separation by gel electrophoresis, the cosmid fragments in the size range of 1500 to 2000 bp are isolated with the QiaExII Gel Extraction Kit (Product No. 20021, Qiagen, Hilden, Germany).

The DNA of the sequencing vector pZero-1, obtained from Invitrogen (Groningen, Holland, Product Description Zero Background Cloning Kit, Product No. K2500-01), is cleaved with the restriction enzyme BamHI (Amersham Pharmacia, Freiburg, Germany, Product Description BamHI, Product No. 27-0868-04). The ligation of the cosmid fragments in the sequencing vector pZero-1 is carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture is then electroporated (Tauch et al. 1994, FEMS Microbiol Letters, 123:343–7) into the *E. coli* strain DH5αMCR (Grant, 1990, Proceedings of the National Academy of Sciences, USA, 87:4645–4649) and plated out on LB agar (Lennox, 1955, Virology, 1:190) with 50 mg/l zeocin.

The plasmid preparation of the recombinant clones is carried out with a Biorobot 9600 (Product No. 900200, Qiagen, Hilden, Germany). The sequencing is carried out by the dideoxy chain termination method of Sanger et al. (1977, Proceedings of the National Academy of Sciences, USA, 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) is used. The separation by gel electrophoresis and analysis of the sequencing reaction are carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained are then processed using the Staden program package (1986, Nucleic Acids Research, 14:217–231) version 97-0. The individual sequences of the pZero1 derivatives are assembled to a continuous contig. The computer-assisted coding region analysis is prepared with the XNIP program (Staden, 1986, Nucleic Acids Research 14:217–231).

The resulting nucleotide sequence is shown in SEQ ID No. 1. Analysis of the nucleotide sequence shows an open reading frame of 840 base pairs, which is called the nadC gene. The nadC gene codes for a protein of 279 amino acids.

Example 3
Preparation of the Shuttle Vector pZ-nadCex for Amplification of the nadC Gene *C. glutamicum*
3.1. Cloning of the nadC Gene From the strain ATCC 13032, chromosomal DNA is isolated by the method of Eikmanns et al. (Microbiology 140: 1817–1828 (1994)). On the basis of the sequence of the nadC gene known for *C. glutamicum* from example 2, the following oligonucleotides are chosen for the polymerase chain reaction. In addition, suitable restriction cleavage sites which allow cloning into the target vector are inserted:

nadC-ex1 shown in SEQ ID No. 3
5' GAT CTA <u>CAA TTC</u> ATG ACT ACC CAT ATT GAC CGC 3' nadC-ex2 shown in SEQ ID No. 4
5' AAG TCT <u>CTG CAG</u> GGT GGC TGC ATT ATC AAG GTA 3'

The primers shown were synthesized by ARK Scientific GmbH Biosystems (Darmstadt, Germany). The primer nadC-ex1 contains the sequence for the cleavage site of the restriction endonuclease EcoRI and the primer nadC-ex2 the cleavage site of the restriction endonuclease PstI, which are marked by underlining in the nucleotide sequence shown above. The PCR reaction is carried out by the standard PCR method of Innis et al. (PCR Protocols. A Guide to Methods and Applications, 1990, Academic Press) with Pwo-Polymerase from Roche Diagnostics GmbH (Mannheim, Germany). With the aid of the polymerase chain reaction, the primers allow amplification of a DNA fragment 890 bp in size, which carries the nadC gene from *Corynebacterium glutamicum* without a potential promoter region. The fragment amplified in this way is tested electrophoretically in a 0.8% agarose gel and checked by sequencing.

The PCR fragment obtained in this manner is cleaved completely with the restriction enzymes EcoRI and PstI and, after separation in a 0.8% agarose gel, isolated from the gel with the QiaExII Gel Extraction Kit (Product No. 20021, Qiagen, Hilden, Germany).
3.2. Cloning of nadC in the Vector pZ8-1

The *E. coli*-*C. glutamicum* shuttle expression vector pZ8-1 (EP 0 375 889) is employed as the base vector for expression both in *C. glutamicum* and in *E. coli*. DNA of this plasmid is cleaved completely with the restriction enzymes EcoRI and PstI and then dephosphorylated with shrimp alkaline phosphatase (Roche Diagnostics GmbH, Mannheim, Germany, Product Description SAP, Product No. 1758250). The nadC fragment isolated from the agarose gel in example 3.1 is mixed with the vector pZ8-1 prepared in this way and the batch is treated with T4 DNA ligase (Amersham Pharmacia, Freiburg, Germany, Product Description T4-DNA-Ligase, Code no.27-0870-04).

The ligation batch is transformed in the E. coli strain DH5βmcr (Hanahan, In: DNA Cloning. A Practical Approach, Vol. 1, IRL-Press, Oxford, Washington D.C., USA). Selection of plasmid-carrying cells was made by plating out the transformation batch on LB agar (Lennox, 1955, Virology, 1:190) with 50 mg/l kanamycin. After incubation overnight at 37° C., recombinant individual clones are selected. Plasmid DNA is isolated from a transformant with the Qiaprep Spin Miniprep Kit (Product No. 27106, Qiagen, Hilden, Germany) in accordance with the manufacturer's instructions and checked by restriction cleavage. The resulting plasmid is called pZ-nadCex. It is shown in FIG. 1.

Example 4

Transformation of the Strain ATCC13032ΔilvA with the Plasmid pZ-nadCex

The strain ATCC13032ΔilvA (=DSM12455) is transformed with the plasmid pZ-nadCex using the electroporation method described by Liebl et al., (FEMS Microbiology Letters, 53:299–303 (1989)). Selection of the transformants takes place on LBHIS agar comprising 18.5 g/l brain-heart infusion broth, 0.5 M sorbitol, 5 g/l Bacto-tryptone, 2.5 g/l Bacto-yeast extract, 5 g/l NaCl and 18 g/l Bacto-agar, which has been supplemented with 25 mg/l kanamycin. Incubation is carried out for 2 days at 33° C.

Plasmid DNA is isolated from a transformant by conventional methods (Peters-Wendisch et al., 1998, Microbiology, 144, 915–927), cleaved with the restriction endonucleases EcoRI and PstI, and the plasmid is checked by subsequent agarose gel electrophoresis. The resulting strain was called ATCC13032ΔilvA/pZ-nadCex or DSM12455/pZ-nadCex.

Example 5

Preparation of Nicotinic Acid

The formation of nicotinic acid by the C. glutamicum strains ATCC13032ΔilvA/pZ8-1 and ATCC13032ΔilvA/pZ-nadCex is tested in medium CGXII (Keilhauer et al., 1993, Journal of Bacteriology, 175:5595–5603), which was supplemented with 25 µg/ml kanamycin and 1 mM L-isoleucine.

This medium is called C. glutamicum test medium in the following. In each case 50 ml of freshly prepared C. glutamicum test medium are inoculated with a 16 hours old preculture of the same medium such that the optical density of the culture suspension ($OD_{580}$) at the start of incubation is 0.1. The cultures are incubated at 30° C. and 130 rpm. After incubation for 48 hours the optical density ($OD_{580}$) of the culture is determined and the cells are then removed by centrifuigation at 5000 g for 10 minutes and the supernatant subjected to sterile filtration.

A Novaspec II photometer from Pharmacia (Freiburg, Germany) is employed at a measurement wavelength of 580 nm for determination of the optical density.

The nicotinic acid in the culture supernatant is quantified by means of Lactobacillus plantarum ATCC 8014 in accordance with the instructions in the handbook of DIFCO (DIFCO MANUAL, 10$^{th}$ Edition, p. 1100–1102; Michigan, USA). Nicotinic acid from Sigma (Deisenhofen, Germany) is used for the calibration.

The result is shown in Table 1.

TABLE 1

| Strain | Cell density $OD_{580}$ | Concentration (ng/ml) |
|---|---|---|
| ATCC13032ΔilvA/pZ8-1 | 12 | 24 |
| ATCC13032ΔilvA/pZ-nadCex | 15 | 35 |

The present application claims priority to German Application No.DE10055870.4 filed Nov. 10, 2000, the entire contents of which are hereby incorporated by reference.

Obviously, numerous modifications and variations on the present invention are possible in light of the above teachings. It is therefore to be understood that within the scope of the appended claims, the invention may be practised otherwise than as specifically described herein.

What is claimed is:

1. An isolated polynucleotide which encodes a protein comprising the amino acid sequence of SEQ ID NO:2.

2. The isolated polynucleotide of claim 1, wherein said protein has nicotinate nucleotide pyrophosphorylase protein activity.

3. An isolated polynucleotide, which comprises SEQ ID NO:1.

4. An isolated polynucleotide which is complimentary to the polynucleotide of claim 3.

5. An isolated polynucleotide which is at least 70% identical to the polynucleotide of claim 3.

6. An isolated polynucleotide which is at least 80% identical to the polynucleotide of claim 3.

7. An isolated polynucleotide which is at least 90% identical to the polynucleotide of claim 3.

8. An isolated polynucleotide which hybridizes under stringent conditions to the polynucleotide of claim 3; wherein said stringent conditions comprise washing in 5×SSC at a temperature from 50 to 68° C.

9. The isolated polynucleotide of claim 3, which encodes a protein having nicotinate nucleotide pyrophosphorylase activity.

10. A primer for a polymerase chain reaction to prepare or amplify a polynucleotide encoding a polypeptide having niconitate nucleotide pyrophosphorylase activity, comprising at least 15 consecutive nucleotides selected from nucleotides 1 to 700 of SEQ ID NO: 1.

11. A vector comprising the isolated polynucleotide of claim 1.

12. A vector comprising the isolated polynucleotide of claim 3.

13. A host cell comprising the isolated polynucleotide of claim 1.

14. A host cell comprising the isolated polynucleotide of claim 3.

15. The host cell of claim 13, which is a Coryneform bacterium.

16. The host cell of claim 14, which is a Coryneform bacterium.

17. The host cell of claim 15, which is *Corynebacterium glutamicum*.

18. The host cell of claim 16, which is *Corynebacterium glutamicum*.

19. A Coryneform bacterium which comprises an enhanced nadC gene.

20. The Coryneform bacterium of claim 19, wherein said nadC gene comprises the polynucleotide sequence of SEQ ID NO: 1.

21. An isolated *Corynebacterium glutamicum* DSM12455/pz-nadCex.

22. An isolated polynucleotide which hybridizes under stringent condition to the polynucleotide of claim 4; wherein said stringent conditions comprise washing in 5×SSC at a temperature from 50 to 68° C.

23. An isolated polynucleotide, comprising at least 15 consecutive nucleotides of the polynucleotide according to claim 3 or a complement thereof, wherein said isolated polynucleotide encodes a polypeptide having nicotinate nucleotide pyrophosphorylase activity.

24. An isolated polynucleotide, consisting of a nucleic acid sequence of from 23 to 300 consecutive nucleotides selected from SEQ ID NO: 1.

25. A process for producing nicotinic acid or a nicotinic acid derivative comprising:
    culturing the host cell of claim 13 in a medium suitable for the expression of the polynucleotide; and collecting the nicotinic acid or nicotinic acid derivative.

26. The process of claim 25, wherein after said collecting the process further comprises a step of concentrating the nicotinic acid or nicotinic acid derivative.

27. The process of claim 25, wherein the host cell further comprises at least one gene whose expression is enhanced, wherein said gene is selected from the group consisting of pyc, zwa1 and prs.

28. The process of claim 27, wherein the enhanced expression of said gene comprises overexpression of the gene.

29. The process of claim 25, wherein the host cell further comprises at least one gene whose expression is attenuated, wherein said gene is selected from the group consisting of pck, poxB and zwa2.

30. A process for producing nicotinic acid or a nicotinic acid derivative comprising:
    culturing the host cell of claim 14 in a medium suitable for the expression of the polynucleotide; and collecting the nicotinic acid or nicotinic acid derivative.

31. The process of claim 30, wherein after said collecting the process further comprises a step of concentrating the nicotinic acid or nicotinic acid derivative.

32. The process of claim 30, wherein the host cell further comprises at least one gene whose expression is enhanced, wherein said gene is selected from the group consisting of pyc, zwa1 and prs.

33. The process of claim 32, wherein the enhanced expression of said gene comprises overexpression of the gene.

34. The process of claim 30, wherein the host cell further comprises at least one gene whose expression is attenuated, wherein said gene is selected from the group consisting of pck, poxB and zwa2.

35. A process for producing nicotinic acid or nicotinic acid derivatives comprising:
    culturing the host cell of claim 19 in a medium suitable for the expression of the polynucleotide; and collecting the nicotinic acid or nicotinic acid derivative.

36. The process of claim 35, further comprising after said collecting a step of concentrating the nicotinic acid or nicotinic acid derivative.

37. The process of claim 35, wherein the host cell further comprises at least one gene whose expression is enhanced, wherein said gene is selected from the group consisting of pyc, zwa1 and prs.

38. The process of claim 37, wherein the enhanced expression of said gene comprises overexpression of the gene.

39. The process of claim 35, wherein the host cell further comprises at least one gene whose expression is attenuated, wherein said gene is selected from the group consisting of pck, poxB and zwa2.

40. A process for screening for polynucleotides which encode a protein having nicotinate nucleotide pyrophosphorylase activity comprising hybridizing a complement of the isolated polynucleotide of claim 1 to the polynucleotide to be screened; expressing the polynucleotide to be screened to produce a protein; and detecting the presence or absence of nicotinate nucleotide pyrophosphorylase activity in said protein.

41. The process of claim 40, wherein said process comprises arrays, microarrays and/or DNA chips.

42. A process for screening for polynucleotides which encode a protein having nicotinate nucleotide pyrophosphorylase activity comprising hybridizing a complement of the isolated polynucleotide of claim 3 or fragments thereof to the polynucleotide to be screened; expressing the polynucleotide to be screened to produce a protein; and detecting the presence or absence of nicotinate nucleotide pyrophosphorylase activity in said protein.

43. The process of claim 42, wherein said process comprises arrays, microarrays and/or DNA chips.

44. A process for screening for polynucleotides which encode a protein having nicotinate nucleotide pyrophosphorylase activity comprising hybridizing the complement of an isolated polynucleotide comprising at least 23 consecutive nucleotides selected from SEQ ID NO: 1 to the polynucleotide to be screened; expressing the polynucleotide to be screened to produce a protein; and detecting the presence or absence of nicotinate nucleotide pyrophosphorylase activity in said protein.

45. The process of claim 44, wherein said process comprises arrays, microarrays and/or DNA chips.

46. A process for screening for polynucleotides which encode a protein having nicotinate nucleotide pyrophosphorylase activity, comprising hybridizing the isolated polynucleotide of claim 4 to the polynucleotide to be screened; expressing the polynucleotide to be screened to produce a protein; and detecting the presence or absence of nicotinate nucleotide pyrophosphorylase activity in said protein.

47. A probe for a hybridization reaction to isolate, detect, or determine if a polynucleotide encodes a polypeptide having niconitate nucleotide pyrophosphorylase activity, comprising at least 23 consecutive nucleotides selected from SEQ ID NO: 1 or a complement thereof.

48. A method of increasing the number of copies of a polynucleotide encoding a polypeptide having nicotinate nucleotide pyrophosphorylase activity, comprising
    contacting a polynucleotide encoding a polypeptide having nicotinate nucleotide pyrophosphorylase activity with an isolated polynucleotide comprising at least 15 consecutive nucleotides selected from nucleotides 1 to 700 of SEQ ID NO: 1.

49. The method according to claim 48, further comprising amplifying the polynucleotide encoding a polypeptide having nicotinate nucleotide pyrophosphorylase activity with an isolated polynucleotide comprising at least 15 consecutive nucleotides selected from nucleotides 1 to 700 of SEQ ID NO: 1.

50. The method according to claim 49, wherein said amplifying is performed by the polymerase chain reaction.

51. The method according to claim 48, further comprising isolating the polynucleotide encoding a polypeptide having nicotinate nucleotide pyrophosphorylase activity.

52. A process for screening for polynucleotides which encode a protein having nicotinate nucleotide pyrophosphorylase activity comprising hybridizing the isolated polynucleotide of claim 4 or fragments thereof to the polynucleotide to be screened; expressing the polynucleotide to be screened to produce a protein; and detecting the presence or absence of nicotinate nucleotide pyrophosphorylase activity in said protein.

* * * * *

SEQUENCE LISTING

<160> NUMBER OF SEQ ID NOS: 4

<210> SEQ ID NO 1
<211> LENGTH: 2270
<212> TYPE: DNA
<213> ORGANISM: Corynebacterium glutamicum
<220> FEATURE:
<221> NAME/KEY: CDS
<222> LOCATION: (701)..(1537)

<400> SEQUENCE: 1

```
cgtgggtgag cacggcggaa ttgtatgcac ctcctcaaat gcacgttccg tattggagtg      60
ggcgtttgaa cgcggccaac gagtcctgtt cttcccgat cagcacttgg gtcgaaacac     120
cgcgaaagcc atgggcattg ggatcgatca aatgcccctg tggaatccca acaaaccact     180
gggtggcaac accgtttccg agctagaaaa cgcaaaggta ctgctctggc atggtttctg     240
ctctgtacac aagcgcttta ctgtcgagca gatcaacaaa gcccgcgccg agtaccccga     300
cgttcacgtc atcgtgcacc ctgaatcccc catgccagtt gttgacgccg ccgactcatc     360
cggatccact gacttcattg tgaaagccat tcaagcagca ccggcaggat ctacctttgc     420
gatcggcacc gaaatcaact tggttcagcg cctggcagcc cagtacccgc agcacaccat     480
```

-continued

```
cttctgcctc gaccctgtca tctgcccatg ctccaccatg tatcgcattc accctggtta        540
cctggcctgg gcacttgagg agttggtggc tggaaacgtg attaaccaga tttctgtctc        600
tgaatccgtg gcggcaccgg cgcgagtcgc tttggaaagg atgctatctg ttgttccagc        660
agctcctgtt actcctagct cctcgaagga tgcgtaattt atg act acc cat att          715
                                             Met Thr Thr His Ile
                                              1               5 gac cgc atc gtt ggc gca gcg tta tcc gag gat gcg cca tgg ggc gac           763
Asp Arg Ile Val Gly Ala Ala Leu Ser Glu Asp Ala Pro Trp Gly Asp
                10              15                  20 att acc tcc gac act ttt atc cca gga tcg gcg cag ctg agc gcc aag           811
Ile Thr Ser Asp Thr Phe Ile Pro Gly Ser Ala Gln Leu Ser Ala Lys
            25                  30                  35 gtt gtt gcc cgg gag cca ggt gtg ttc agc ggg cag gcg ctt ttc gac           859
Val Val Ala Arg Glu Pro Gly Val Phe Ser Gly Gln Ala Leu Phe Asp
            40                  45                  50 gcc tcc ttc cgg ctc gtc gat cct agg ata aac gca tcc ctt aag gtg           907
Ala Ser Phe Arg Leu Val Asp Pro Arg Ile Asn Ala Ser Leu Lys Val
    55                  60                  65 gct gat ggt gac agc ttt gaa acc ggg gac atc cta gga aca att acc           955
Ala Asp Gly Asp Ser Phe Glu Thr Gly Asp Ile Leu Gly Thr Ile Thr
70                  75                  80                  85 ggc agt gct aga agc atc ctc cgt tca gag cgc att gct ctc aac ttc          1003
Gly Ser Ala Arg Ser Ile Leu Arg Ser Glu Arg Ile Ala Leu Asn Phe
                90                  95                  100 att cag agg acg tcc ggc atc gct aca ttg aca tcg tgc tat gtt gca          1051
Ile Gln Arg Thr Ser Gly Ile Ala Thr Leu Thr Ser Cys Tyr Val Ala
            105                 110                 115 gag gtt aaa ggc acc aaa gcc cgc att gtt gat acc cgg aaa acc aca          1099
Glu Val Lys Gly Thr Lys Ala Arg Ile Val Asp Thr Arg Lys Thr Thr
            120                 125                 130 ccc ggc ctg cgc atc att gaa cgc caa gct gtc cgt gac ggt ggc gga          1147
Pro Gly Leu Arg Ile Ile Glu Arg Gln Ala Val Arg Asp Gly Gly Gly
    135                 140                 145 ttt aat cac cga gcc acc ttg tcc gat gct gtc atg gtg aaa gat aac          1195
Phe Asn His Arg Ala Thr Leu Ser Asp Ala Val Met Val Lys Asp Asn
150                 155                 160                 165 cat ctc gca gcc atc gca tcc cag ggg ctc agc atc act gaa gcg ctg          1243
His Leu Ala Ala Ile Ala Ser Gln Gly Leu Ser Ile Thr Glu Ala Leu
                170                 175                 180 tcg aat atg aaa gct aaa ctc ccc cac acc acc cat gtg gaa gtc gaa          1291
Ser Asn Met Lys Ala Lys Leu Pro His Thr Thr His Val Glu Val Glu
            185                 190                 195 gtt gat cat ata gag cag atc gaa cca gtt ctt gct gct ggt gtg gac          1339
Val Asp His Ile Glu Gln Ile Glu Pro Val Leu Ala Ala Gly Val Asp
            200                 205                 210 acc atc atg ttg gat aat ttc acc att gat cag ctc atc gaa ggc gtt          1387
Thr Ile Met Leu Asp Asn Phe Thr Ile Asp Gln Leu Ile Glu Gly Val
    215                 220                 225 gat ctc att ggt gga cgt gca ctg gtg gaa gca tct ggc gga gtc aac          1435
Asp Leu Ile Gly Gly Arg Ala Leu Val Glu Ala Ser Gly Gly Val Asn
230                 235                 240                 245 ctc aac acc gcg gga aag att gca tca acc ggt gtc gac gtc att tcc          1483
Leu Asn Thr Ala Gly Lys Ile Ala Ser Thr Gly Val Asp Val Ile Ser
            250                 255                 260 gtt gga gcg ctt acc cat tct gtg cat gca ctt gac cta gga ctc gat          1531
Val Gly Ala Leu Thr His Ser Val His Ala Leu Asp Leu Gly Leu Asp
            265                 270                 275
```

-continued

| | |
|---|---|
| att ttc taatgctcta ccttgataat gcagccacca ccagtgtgcg caatgaagca | 1587 |
| Ile Phe | |
| cttgaggcca tgtggcctta tctcaccgga gcgtttggca atccgtcaag tccccatgag | 1647 |
| gtgggaagac tcgcctctgc ggggctggag gatgctcgaa ctcgggtggc ccgcattatc | 1707 |
| ggaggacgcc ccacacaggt gacgtttacg tcgggtggat cagaagccaa caacctcgct | 1767 |
| atcaaggag cgtgcttagc taatcctcgt ggccggcacc tcatcaccac cccgatcgag | 1827 |
| catgacagtg tcctagaaac tgctgcttat cttgaaaggt ttcatgattt cgagatcacc | 1887 |
| tacctatccc ccgatcacac tgggctgatc tccccggagg gtctccgcaa agcagtcagg | 1947 |
| ccggacacca cattgatcag cattggttat gccaacaatg aggtgggaac cattcagccg | 2007 |
| atagctgagt tggcggcggt aagcagtacg ccttttcaca ccgatgcagt gcaagctgca | 2067 |
| catttaaccct ttgacttggg agttgacgcg ttaagtttgt cgggtcataa attcggtgcg | 2127 |
| cctaagggga ttggagtgtt atggtcaaag cttcccctgg agccggtaat ccatggcggc | 2187 |
| ggccaggaaa aagggcggcg tagtggcacg gaaaacgttg cgggggctat cgccttgcc | 2247 |
| actgccttgg aattggccag ggc | 2270 |

<210> SEQ ID NO 2
<211> LENGTH: 279
<212> TYPE: PRT
<213> ORGANISM: Corynebacterium glutamicum

<400> SEQUENCE: 2

```
Met Thr Thr His Ile Asp Arg Ile Val Gly Ala Ala Leu Ser Glu Asp
1               5                   10                  15

Ala Pro Trp Gly Asp Ile Thr Ser Asp Thr Phe Ile Pro Gly Ser Ala
            20                  25                  30

Gln Leu Ser Ala Lys Val Val Ala Arg Glu Pro Gly Val Phe Ser Gly
        35                  40                  45

Gln Ala Leu Phe Asp Ala Ser Phe Arg Leu Val Asp Pro Arg Ile Asn
    50                  55                  60

Ala Ser Leu Lys Val Ala Asp Gly Asp Ser Phe Glu Thr Gly Asp Ile
65                  70                  75                  80

Leu Gly Thr Ile Thr Gly Ser Ala Arg Ser Ile Leu Arg Ser Glu Arg
                85                  90                  95

Ile Ala Leu Asn Phe Ile Gln Arg Thr Ser Gly Ile Ala Thr Leu Thr
            100                 105                 110

Ser Cys Tyr Val Ala Glu Val Lys Gly Thr Lys Ala Arg Ile Val Asp
        115                 120                 125

Thr Arg Lys Thr Thr Pro Gly Leu Arg Ile Ile Glu Arg Gln Ala Val
    130                 135                 140

Arg Asp Gly Gly Gly Phe Asn His Arg Ala Thr Leu Ser Asp Ala Val
145                 150                 155                 160

Met Val Lys Asp Asn His Leu Ala Ala Ile Ala Ser Gln Gly Leu Ser
                165                 170                 175

Ile Thr Glu Ala Leu Ser Asn Met Lys Ala Lys Leu Pro His Thr Thr
            180                 185                 190

His Val Glu Val Glu Val Asp His Ile Glu Gln Ile Glu Pro Val Leu
        195                 200                 205

Ala Ala Gly Val Asp Thr Ile Met Leu Asp Asn Phe Thr Ile Asp Gln
    210                 215                 220

Leu Ile Glu Gly Val Asp Leu Ile Gly Gly Arg Ala Leu Val Glu Ala
225                 230                 235                 240
```

-continued

```
Ser Gly Gly Val Asn Leu Asn Thr Ala Gly Lys Ile Ala Ser Thr Gly
                245                 250                 255

Val Asp Val Ile Ser Val Gly Ala Leu Thr His Ser Val His Ala Leu
            260                 265                 270

Asp Leu Gly Leu Asp Ile Phe
            275

<210> SEQ ID NO 3
<211> LENGTH: 33
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA-primer nadC-ex1

<400> SEQUENCE: 3
gatctagaat tcatgactac ccatattgac cgc                              33

<210> SEQ ID NO 4
<211> LENGTH: 33
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA-primer nadC-ex2

<400> SEQUENCE: 4
aagtctctgc agggtggctg cattatcaag gta                              33
```